United States Patent [19]

Leston

[11] Patent Number: 4,469,900

[45] Date of Patent: Sep. 4, 1984

[54] COMPLEX FORMED FOR SEPARATING CHLORINATED PHENOLS

[75] Inventor: Gerd Leston, Pittsburgh, Pa.

[73] Assignee: Koppers Company, Inc., Pittsburgh, Pa.

[21] Appl. No.: 567,957

[22] Filed: Jan. 4, 1984

Related U.S. Application Data

[62] Division of Ser. No. 372,060, Apr. 26, 1982, Pat. No. 4,429,168.

[51] Int. Cl.$^3$ ............................................. C07C 39/24
[52] U.S. Cl. ................................... 568/774; 568/701; 568/702
[58] Field of Search ....................... 568/774, 701, 702

[56] References Cited

U.S. PATENT DOCUMENTS 4,366,329  12/1982  Raynold et al. .................... 568/755
4,429,168   1/1984  Leston ................................. 568/755

OTHER PUBLICATIONS

Sharpless et al., "Jour. Org. Chem", vol. 40, No. 9, (1975), 1252–1257.

*Primary Examiner*—Werren B. Lone
*Attorney, Agent, or Firm*—Daniel J. Long; Herbert J. Zeh, Jr.

[57] ABSTRACT

A process is disclosed for separating closely-boiling chlorinated phenolic compounds from other chlorinated and unchlorinated phenolics by treating a mixture of the phenolics with a metal halide salt. The metal halide salt preferentially forms a complex with one of the phenolics over other related closely-boiling phenolics in the mixture. The preferentially-formed complex of one of the phenolics may then be isolated from the mixture and the complex decomposed to provide a product substantially enriched in, or substantially entirely composed of, one phenolic. The process is particularly suitable for resolving a mixture comprising phenol or cresol from their closely-boiling ortho-chlorinated derivatives, or a mixture of two isomeric chlorinated phenols or cresols or a mixture of closely-boiling mono- and dichlorinated phenols or cresols.

6 Claims, No Drawings

COMPLEX FORMED FOR SEPARATING CHLORINATED PHENOLS

This is a division of application Ser. No. 372,060, filed Apr. 26, 1982, now U.S. Pat. No. 4,429,168.

BACKGROUND OF THE INVENTION

1. Field of the Invention

Preferential complexation of one organic compound in a mixture of related compounds is a known technique for resolving mixtures of compounds having close boiling points. Of particular interest herein are methods for resolving mixtures of phenolic compounds, at least one of which is a chlorinated phenolic, by preferential complexation of one of the phenolics.

2. State of the Art

Mixtures of chlorinated phenolics are available as end-products or by-products of many commercial chlorination reactions involving the ring chlorination of phenol and cresols. Such reactions produce many closely-boiling chlorinated phenolics. The isolation and purification of individual chlorinated phenolics is very difficult by the use of conventional separation methods such as fractional distillation.

There are chemical processes known for separating closely-boiling organic compounds by methods other than, or in addition to, energy-intensive physical separation techniques such as fractional distillation or fractional crystallization. These chemical processes involve a step of preferential complexation of one component of a mixture of closely-boiling compounds over other components of the mixture. For example, U.S. Pat. No. 4,267,389 to Leston, describes treating a phenolic mixture comprising para-cresol, methylated phenols and ethylated phenols, with an inorganic halide salt, such as calcium bromide, to remove para-cresol from the mixture. Removal of para-cresol from the mixture involves formation of a complex between para-cresol and calcium bromide, which complex forms preferentially over complexes between calcium bromide and other components of the phenolic mixture.

Mixtures of various alcohols may be resolved by treatment with a halide salt. For example, in Sharpless et al., *J. Org. Chem.*, Vol. 40, No. 9, p.p. 1252–1257 (1975), there is reported a study of competition between pairs of mono-hydroxy alcohols and mono-hydroxy phenols for complex formation with a halide salt. This study finds that phenols as a class form poorer complexes then alcohols of comparable melting point, probably because the phenols are weaker bases than the comparable alcohols.

There remains need, therefore, for methods for resolution of mixtures of closely-boiling chlorinated phenolics by chemical complexation methods, rather than by fractional crystallization or distillation.

SUMMARY OF THE INVENTION

A mixture of two or more phenolics some or all of which are chlorinated, may be resolved into individual phenolic components by a process involving a step of forming a solid complex preferentially between a metal halide salt and one of the phenolics in the mixture containing at least one chlorinated phenolic. A metal halide salt suitable for forming the solid complex may be selected from the group consisting of calcium bromide, calcium chloride, lithium bromide, magnesium chloride and magnesium bromide. Resolution of such phenolic mixture may be accomplished by either of the following two preferred methods.

A first method involves bringing together a mixture of two or more phenolics at least one or more of which is a chlorinated phenolic, and a selected metal halide salt, the metal halide being selected such that a complex forms with one of the phenolics in preference to, or preferentially over, other phenolics in the mixture. This preferentially formed complex constitutes a solid material in contact with a liquid phase such as provided by aliphatic, alicyclic and aromatic hydrocarbons, and their chlorinated derivatives, ethers, esters and ketones. Also, any combination of such solvents may be used. Alcohols are specifically excluded as solvents inasmuch as they form complexes with the metal halide salt solvent. The solid complex may then be removed or isolated from the liquid phase and thereafter decomposed to a product comprising a predominantly greater amount of the preferentially-complexed phenolic than other phenolics, as compared to the relative amounts of phenolics present in the original mixture. The product may also contain phenolic derived from complexes which form with the selected metal halide salt, but in lesser amount than the amount of phenolic derived from the preferentially-formed complex.

A second method involves forming a mixture of two or more phenolics, at least one of which is a chlorinated phenolic, in contact with a selected metal halide salt, the metal halide salt initially present in an amount relative to one phenolic and selected such that one or more complexes form between the selected metal halide salt and one or more of the phenolics, but such that at least one of the phenolics forms no complex or forms a significantly lesser amount of complex with the selected metal halide salt than the preferentially-complexed phenolic. This phenolic which forms no complex, or which forms a complex in a significantly lesser amount than other phenolics, relative to amounts of phenolics originally present in the mixture, remains dissolved in the liquid phase. The solvent providing the liquid phase may then be removed or isolated from the preferentially-complexed phenolics which are present as solid material. Removal of the solvent provides a product containing an enriched amount of the phenolic which did not preferentially complex with the selected metal halide salt, as compared to the original mixture of phenolics.

One advantage provided by the process of the invention is good resolution or mutual separation of pairs of phenolics can be obtained from a mixture of two or more phenolics which have boiling points in a relatively narrow range, 5°–8° C., which separation would be substantially impossible to accomplish in a one-stage fractional distillation or separation. A second advantage resides in this chemical-separation process requiring significantly less energy to accomplish good resolution of closely-boiling phenolics than physical-separation methods such as fractional distillation or crystallization.

The chemical-separation process of the invention may also be used advantageously in conjunction with conventional physical-separation processes. For example, calcium bromide complexation may be used in an initial treatment of a phenolic mixture for separating the closest-boiling compounds, that is, compounds boiling within a range of five centigrade degrees. Then, a resulting mixture of compounds having boiling points differing by more than five centigrade degrees can be treated by distillation or crystallization for more complete resolution of the mixture.

DETAILED DESCRIPTION OF THE INVENTION

The term "phenolic" or "phenolics" as used herein includes phenol, cresols and ring-chlorinated derivatives of phenol and cresols. The term "ring-chlorinated derivative" as used herein designates a phenolic wherein one or more of the hydrogens on the aromatic ring is replaced by chlorine. The phases "resolving a mixture of phenolics" and "resolution of a mixture of phenolics" relate to a mechanism or a result in which the individual phenolic components of a mixture containing two or more phenolics may be separated or isolated from each other. Thus, the separation of a significant amount of one phenolic from a mixture of two phenolics constitutes a resolution of the mixture. The phrases also embrace separation of a multi-component mixture into groups of phenolics, each group containing two or more phenolics. Also included within the definition are treatments resulting in a significant increase in the amount of one or more phenolics as compared to the composition of the original mixture of phenolics, even where the original mixture contained relatively small amounts of the enriched phenolic. It is contemplated that a differentiation or enrichment in the relative amounts of phenolics is a "significant enrichment" if treatment of a mixture provides an increase of at least about 20 weight percent in one or more of the phenolics as compared to the composition of the original mixture.

The phrases "preferentially-formed complex" and "predominantly-complexed phenolic" are intended as abbreviated descriptions of the complex comprising a selected metal halide salt and a dihydric phenol which forms in an amount significantly greater than an amount of any other complex of another phenolic resulting from treatment of the phenolic mixture with the selected metal halide salt. Any complex formed will preferably be comprised substantially entirely of a complex of a single type of phenolic. It is recognized, however, that other phenolics in a starting mixture may form complexes with the selected salt in secondary or lesser amounts than the primary, predominantly-formed complex. Such secondary complex formation in lesser amounts is not deleterious provided that the ratio of the predominant complex to the secondary complex in the resulting solid material is sufficiently high to provide a useful resolution of a phenolic mixture. It is contemplated that a primary/secondary or predominant/lesser ratio of the relative amounts of complexes of the treated mixture constitutes a significant and usefully-resolved mixture of phenolics.

Mixtures of phenolics susceptible to treatment with the process of the invention include mixtures of two or more phenolics, one or more of which is chlorinated, such as phenol, o-chlorophenol, m-chlorophenol, p-chlorophenol, 2,6-dichlorophenol, 2,4-dichlorophenol, 2,4,6-trichlorophenol, m-cresol, 2-chloro-m-cresol, 6-chloro-m-cresol, 4-chloro-m-cresol, 5-chloro-m-cresol, 2,4-dichloro-m-cresol, 2,6-dichloro-m-cresol, 4,6-dichloro-m-cresol, 2,4,6-trichloro-m-cresol, p-cresol, 2-chloro-p-cresol, 3-chloro-p-cresol, 2,6-dichloro-p-cresol, o-cresol, 6-chloro-o-cresol, 4-chloro-o-cresol and 4,6-dichloro-o-cresol.

The family of metal halide salts which may be used in the invention are characterized in having several features in common. For example, in addition to each member of the family being an inorganic salt of a metallic chloride or bromide, these halide salts are characterized in taking on water of hydration. The hydratable nature of these metal halide salts is believed to be significant in the mechanism of complex formation with the phenolics, even though no water is involved in the complexation reaction. Of the family of metal halide salts suitable for use in the invention, calcium bromide is preferred. It is also preferred, whether calcium bromide or calcium chloride or any other of the halide salts is used, that the salt have a water content, either as hydrate or occluded, of less than about ten weight percent. Also, it is preferred that the salt have a particle size less than about 200 mesh.

Solvents which may be used in the complexation reaction include those organic compounds which dissolve the phenolic mixtures but do not preferentially react with the metal halide salt. Solvents suitable include aliphatic, alicyclic and aromatic hydrocarbons, their chlorinated derivatives, ethers, esters and ketones. Alcohols are specifically excluded since they may form complexes with the metal halide salt. Mixtures of solvents may also be used.

The process of the invention is particularly suitable for resolving mixtures of close-boiling phenolics, one or more of which is a chlorinated phenolic. Examples of such mixtures include the following: phenol (b.p 182°) and o-chlorophenol (b.p. 176°); m-chlorophenol (b.p. 216.7°) and p-chlorophenol (b.p. 217°–219°); p-chlorophenol and 2,4-dichlorophenol (b.p. 209°) m-cresol (b.p. 202°), 2-chloro-m-cresol (b.p. 198°–9°) and 6-chloro-m-cresol (b.p. 197°–8°); 4-chloro-m-cresol (b.p. 234°–6°) and 4,6-dichloro-m-cresol (b.p. 235°–6°); p-cresol (b.p. 201.8°) and 2-chloro-p-cresol (b.p. 196°). Generally, in a mixture containing the parent unchlorinated phenolic and its closely-boiling ortho-chlorinated phenolic derivative, the unchlorinated phenol is preferentially complexed with calcium bromide. Generally, in a mixture containing an ortho-chorinated phenolic and a para-chlorinated phenolic, the para-chlorinated phenolic is preferentially complexed. Generally, in a mixture containing a para-chlorinated phenolic and its ortho-para-dichlorinated derivative, the para-chlorinated phenolic is preferentially complexed with calcium bromide. Generally, in a mixture of isomeric meta- and para-chlorinated phenols, the para-isomer is preferentially complexed.

Generally, the halide salt is added to the mixture of phenolics dissolved in, or in contact with, a solvent. For calcium bromide, for example, the salt is preferably added in amount in a range from about 0.1 mole to about 4 moles to one mole of the phenolic to be preferentially complexed. Usually, the complexation reaction takes place in the presence of a catalyst such as a lower aliphatic alcohol. A typical catalytic amount of the alcohol would be approximately five mole percent of the alcohol based on the total phenolic content.

After the aforementioned components are brought together as a mixture, usually in the form of a slurry, the mixture is agitated for a period of time sufficient for the phenolic-metal halide salt complex to form. A typical mixing time is in a range from about one hour to about 24 hours. Mixing is typically conducted at room temperature and at atmospheric pressure, although the complexation reaction may be conducted at practically any temperature in a range from about 0° C. to about 150° C. Superatmospheric pressure may be used to avoid escape of reactants and solvents. Also, care must be taken to exclude ambient moisture from the reaction mixture.

After the mixing period, the mixture contains a fluffy, white or gray solid material component in contact with a liquid component. The solid material may be separated from the liquid component by any conventional separation techniques such as by decanting, by centrifugation, or by filtration. If filtration is used to separate the solid material from the liquid, the filtration may be conducted with the aid of pressure gradient applied across the filter medium. The separated solid material may be washed with small portions of solvent, and the washings thereafter may be combined with the filtrate. After the washing step, the separated solid material may be optionally dried, usually by means of low heat or in a desiccator under reduced pressure. The drying step is carried out until the solid material reaches a constant weight.

The solid material, which contains the phenolic-metal halide salt complex, is then decomposed to provide the desired phenolic. Decomposition may be accomplished by hydrolysis of the complex in water, by heating of the complex at a temperature usually in a range of from about 150° C. to about 350° C., or by treatment with an alcohol, such as a lower boiling aliphatic alcohol. Preferred decomposition methods include water hydrolysis and heat treatment of the complex. In decomposition of the complex by water hydrolysis, the phenolic may be recovered by treating the water with an organic solvent, typically ether. In decomposition of the complex with heat, the phenolic may be separated by filtration, centrifugation or distillation from the metal halide salt residue. In either of these decomposition methods, the metal halide salt may be recovered and recycled for treatment of another mixture of phenolics, or for subsequent treatment of the separated phenolics in the event of incomplete separation of the mixture of phenolics.

It is an important feature of the invention that the liquid portion of the mixture treated with the metal halide salt contains the phenolic which less predominantly forms a complex with the metal halide salt or which forms substantially no complex with the metal halide salt. Thus the liquid portion of the treated mixture will be enriched in this phenolic and depleted in the phenolic which predominantly complexes with the metal halide salt. This phenolic may be recovered from this liquid portion by conventional distillation or fractionation techniques.

In order to demonstrate the invention a series of individual chlorinated phenolics was treated with calcium bromide to show the formation of a chlorinated phenolic-CaBr$_2$ complex as described in Examples I-IV and Table I. In the working examples which follow, the extracted-and-decomposed complexes of the separated solid material and the liquid portion were subjected to NMR, IR or gas chromatographic analysis to determine the relative amounts of phenolics in the solid material and in the liquid filtrate.

EXAMPLE I

A reaction vessel equipped with stirring means was charged with 12.9 g o-chlorophenol (100 mmole), 0.2 ml absolute ethanol. To the reaction vessel was added 5.0 g powdered anhydrous calcium bromide (25 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. A complexation reaction was run by stirring this mixture for about 1.5 hours at room temperature, after which time 55 ml hexane was added over a 4.5 hour mixing period. Thereafter, the mixture was stirred about 13 more hours. The mixture was observed to contain a large amount of fluffy, white solid material suspended in the liquid solution. The mixture was filtered under suction, in a manner to minimize exposure of the mixture in ambient moisture, so as to separate the fluffy solid material from the liquid component. The separated solid material was washed with small portions of hexane and the hexane washings were combined with the filtrate. The washed solid material was dried in a desiccator under a pressure of 1 mm Hg absolute for a period of time until a substantially constant weight of 6.1 g was recorded. Inasmuch as the dried solid material weighed 6.1 g, it was determined that 1.1 g o-chlorophenol complexed with the calcium bromide so that the molar ratio of o-chlorophenol:calcium bromide in the complex was 0.34:1. Concentration of the filtrate yielded 10.8 g of residue found to be o-chlorophenol.

EXAMPLE II

A complexation reaction was run generally as described in Example I with a mixture of 12.9 g p-chlorophenol (100 mmole), 0.1 ml absolute ethanol, 40 ml toluene and 5.0 g powdered anhydrous calcium bromide (25 mmole). After the mixture was stirred for 1.25 hours at room temperature, another 60 ml toluene was added. Stirring continued for a total of 18 hours. A washed-and-dried solid material was obtained in an amount of 7.35 g. The filtrate was extracted with 10 percent aqueous NaOH, the aqueous solution was acidified with HCl, extracted with diethyl ether, and thereafter concentrated to a residue of 10.3 g recovered p-chlorophenol.

EXAMPLE III

A complexation reaction was run generally as described in Example I with a mixture of 12.9 g m-chlorophenol (100 mmole), 0.2 ml absolute ethanol and 5.0 g powdered anhydrous calcium bromide (25 mmole). After the mixture was stirred for 45 minutes at room temperature, 90 ml hexane was added over the next 40 minutes. A washed-and-dried solid material was obtained in an amount of 10.8 g. Concentration of the filtrate yielded 9.4 g.

EXAMPLE IV

A complexation reaction was run generally as described in Example I with a mixture of 16.5 g 2,4-dichlorophenol (100 mmole), 0.2 ml absolute ethanol, 45 ml toluene and 5.0 g powdered anhydrous calcium bromide (25 mmole). After the mixture was stirred for about 60 hours, a washed-and-dried solid material was obtained in an amount of 5.5 g. Treatment of the filtrate, as described in Example II, yielded 15.7 g recovered 2,4-dichlorophenol.

EXAMPLE V

A complexation reaction was run generally as described in Example I with a mixture of 14.3 g 4-chloro-m-cresol (100 mmole), 0.2 ml absolute ethanol, 105 ml toluene and 5.0 g powered anhydrous calcium bromide. After an 18-hour mixing period, a washed-and-dried solid material was obtained in an amount of 10.1 g.

Treatment of the filtrate as describe in Example II yielded 9.3 g recovered 4-chloro-m-cresol.

EXAMPLE VI

A complexation reaction was run generally as described in Example V with 6-chloro-m-cresol. A solid was obtained weighing 5.2 g.

TABLE I

| Example No. | Phenol | Starting Phenol/CaBr$_2$ Molar Ratio | Phenol/CaBr$_2$ Molar Ratio in Complex |
|---|---|---|---|
| I | o-chlorophenol | 4.0 | 0.34 |
| II | p-chlorophenol | 4.0 | 0.73 |
| III | m-chlorophenol | 4.0 | 1.8 |
| IV | 2,4-dichlorophenol | 4.0 | 0.1 |
| V | 4-chloro-m-cresol | 4.0 | 1.4 |
| VI | 6-chloro-m-cresol | 4.0 | 0.06 |

As shown in Examples VII to XIII, various synthetic mixtures of phenolics, containing one or more chlorinated phenolics, were prepared for treatment with calcium bromide to show the preferential complexation of one phenolic over another phenolic, so as to allow separation of two or more phenolics. In the working examples which follow, the extracted-and-decomposed complexes of the separated solid material and the liquid portions were subjected to GC or IR analysis to determine the relative amounts of the phenolics in the solid material and in the liquid filtrate.

EXAMPLE VII

A reaction vessel equipped with stirring means was charged with 7.15 g 6-chloro-m-cresol (50 mmole) and 5.40 g m-cresol (50 mmole) along with about 0.2 ml absolute ethanol and 90 ml hexane as a solvent for the phenolics to form a solution. To the reaction vessel, there was added 10.0 g finely-ground anhydrous CaBr$_2$ (50 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. During the first hour of mixing, 75 ml hexane was added to the mixture. Then, the mixture was stirred for about 15 more hours at room temperature after which time there was observed a large amount of a fluffy, white solid material suspended in the liquid solution. Then the mixture was filtered under suction, in a manner to minimize exposure of the mixture to ambient moisture, to separate the fluffy solid material from the liquid component. The separated solid was washed twice with 10 ml portions of hexane, the washings then combined with the filtrate. The washed solid was dried in a desiccator under a pressure of 1 mm Hg absolute for two hours at room temperature. The dried solid amounted to 14.55 g, a portion of which was hydrolyzed in water to form a hydrolyzate, which hydrolyzate was extracted from the water by five sequential treatments of the water containing the hydrolyzate with ether. GC analysis of the ether extract derived from the precipitate showed that the solid material contained substantially entirely a complex of m-cresol and calcium bromide, Analysis of the filtrate showed predominantly 6-chloro-m-cresol as the phenolic present. Analytical data are summarized in Table II.

EXAMPLE VIII

A complexation reaction was run as generally described in Example VII with a starting mixture of 1.78 g 6-chloro-m-cresol (12.5 mmole), 2.23 g 4,6-dichloro-m-cresol (50 mmole), 0.2 ml absolute ethanol, 60 ml hexane and 10.0 g powered anhydrous calcium bromide. After the mixture was stirred for about 16 hours at room temperature, a washed-and-dried solid material was obtained in an amount of 2.5 g. Then 1.78 g 4-chloro-m-cresol was added to the filtrate in the presence of 125 ml hexane. The dried solid was added to the filtrate and the mixture was stirred for about 60 hours. A washed-and-dried complex amounting to 4.06 g was obtained. Results of analysis of the hydrolyzed complex and the filtrate are shown in Table II.

EXAMPLE IX

A complexation reaction was run as generally described in Example VII with a starting mixture of 8.16 g 2,4-dichlorophenol (50 mmole), 6.42 g p-chlorophenol (50 mmole), 0.2 ml absolute ethanol, 50 ml toluene and 10.0 g powdered anhydrous calcium bromide (50 mmole). After a three-hour mixing period 70 ml toluene was added. Then the mixture was stirred for 24 total hours at room temperature, filtered and washed with solvent. The solid was dried and amounted to 14.99 g. The filtrate was treated by base-extraction, acidification and then re-extraction with ether. GC analyses of the hydrolyzed solid and the filtrate are shown in Table II.

EXAMPLE X

A complexation reaction was run as described in Example IX except that the mixture was stirred for 22 hours at about 100° C. A washed-and-dried complex weighed 10.8 g and recovered filtrate residue weighed 13.7 g. Results of GC analyses of hydrolyzed complex and the filtrate residue are shown in Table II.

EXAMPLE XI

A complexation reaction was run as generally described in Example VII with a starting mixture of 6.45 g o-chlorophenol (50 mmole), 4.65 g phenol (50 mmole), 0.2 ml absolute ethanol, 80 ml hexane and 5.50 g powdered anhydrous calcium bromide (50 mmole). After 5 hours of mixing, 35 ml hexane was added. The mixture was stirred for about 22 hours more at room temperature. A washed-and-dried solid material was obtained in an amount of 14.71 g and a residue from the filtrate was obtained in an amount of 6.35 g. Results of GC analysis of the hydrolyzed solid and the filtrate are summarized in Table II.

EXAMPLE XII

A complexation reaction was run as generally described in Example VII with a starting mixture of 6.43 g m-chlorophenol (50 mmole), 6.43 g p-chlorophenol (50 mmole), 0.2 ml absolute ethanol, 50 ml toluene and 10.0 g powdered anhydrous calcium bromide (50 mmole). During the first four hours of mixing, 140 ml toluene was added to the mixture. The mixture was stirred for about 24 hours at room temperature. A washed-and-dried solid material was obtained in an amount of 13.6 g and treatment of the filtrate yielded a residue in an amount of 9.2 g. Results of GC analyses of the hydrolyzate and filtrate are summarized in Table II.

TABLE II

COMPETITIVE COMPLEXING OF CHLORINATED PHENOLS

| Example | Phenolics | Starting Mixture Phenol/Phenol/CaBr$_2$ Molar Ratio | Percent of Total Feed Complexed | Feed | Phenol Ratios by GC, Area Ratio Analyses Complex | Filtrate |
|---|---|---|---|---|---|---|
| VII | m-cresol/ 6-chloro-m-cresol | 1:1:1 | 36 | 43.6/56.4 | 98.7/1.3 | 11.0/89.0 |
| VIII | 6-chloro-m-cresol/ 4-chloro-m-cresol/ 4,6-dichloro-m-cresol | 1:1:1:1 | 27 | — | 0/100/0 | 42.9/6.5/50.6 |
| IX | p-chlorophenol[1]/ 2,4-dichlorophenol | 1:1:1 | 52 | 45.4/56.4 | 52.9/47.1 | 29.0/71/0 |
| X | p-chlorophenol/ 2,4-dichlorophenol | 1:1:1 | 5.5 | 45.4/54.6 | 83.8/16.2 | 47.6/52/4 |
| XI | phenol/ o-chlorophenol | 1:1:1 | 43 | 45.9/54.1 | 96.7/3.3 | 1.8/98.2 |
| XII | m-chlorophenol/ p-chlorophenol | 1:1:1 | 31 | 50.0/50.0[2] | 22/78[2] | 59/41 |

[1]This reaction was performed at 100° instead of 25°.
[2]Analyses by infrared spectroscopy.

EXAMPLE XIII

Four grams of chlorine was bubbled through a stirred solution of 10.8 g of p-cresol (10 mmoles) in 100 ml of carbon tetrachloride for about 30 minutes. A five-gram sample, removed and analyzed showed 46.9% p-cresol and 53.1% 2-chloro-p-cresol. Then 0.1 ml of ethanol and 10.00 g powdered anhydrous calcium bromide were added to the chlorinated p-cresol mixture. The mixture was stirred in the absence of atmospheric moisture for about 16 hours. A washed-and-dried solid was obtained weighing 10.40 g. A sample of the solid was hydrolyzed by water and extracted five times with carbon tetrachloride. GC analysis of the combined extract gave 96.6% p-cresol and 3.3% 2-chloro-p-cresol, showing substantially complete separation of p-cresol from its chlorinated derivative by complexation with calcium bromide.

Although specific examples of the instant invention have been set forth hereinabove, it is not intended that the invention be limited solely thereto, but is to include all the variations and modifications falling within the scope of the appended claims.

What is claimed is:

1. A complex consisting essentially of o-chlorophenol and calcium bromide.

2. A complex consisting essentially of p-chlorophenol and calcium bromide.

3. A complex consisting essentially of m-chlorophenol and calcium bromide.

4. A complex consisting essentially of 2,4-dichlorophenol and calcium bromide.

5. A complex consisting essentially of 6-chloro-m-cresol and calcium bromide.

6. A complex consisting essentially of 4-chloro-m-cresol and calcium bromide.

* * * * *